United States Patent [19]

Nauflett

[11] Patent Number: 4,513,148

[45] Date of Patent: Apr. 23, 1985

[54] METHOD FOR THE PREPARATION OF METHYLNITRAMINE

[75] Inventor: George W. Nauflett, Oxon Hill, Md.

[73] Assignee: The United States of America as represented by the Secretary of the Navy, Washington, D.C.

[21] Appl. No.: 394,084

[22] Filed: Jul. 1, 1982

[51] Int. Cl.$^3$ ............................................. C07C 111/00
[52] U.S. Cl. ....................................... 564/109; 564/33; 564/107
[58] Field of Search ........................... 564/33, 107, 109

[56] References Cited

U.S. PATENT DOCUMENTS

| | | | |
|---|---|---|---|
| 2,856,429 | 10/1958 | Sauer | 564/109 |
| 2,997,501 | 8/1961 | Shiino et al. | 564/33 |
| 3,098,872 | 7/1963 | Weakley et al. | 564/33 |

*Primary Examiner*—Robert V. Hines
*Attorney, Agent, or Firm*—Robert F. Beers; Kenneth E. Walden; John C. LaPrade

[57] ABSTRACT

The invention is an improved process for the production of methylnitramine by nitrating dimethylurea with a mixture of sulfuric acid and nitric acid with subsequent separation of 1,3-dimethyl-1,3-dinitrourea by the use of a suitable solvent with recovery of a dimethyl dinitrourea in organic solvent, with hydrolysis of the dimethyldinitrourea with hot water to yield methylnitramine.

12 Claims, No Drawings

METHOD FOR THE PREPARATION OF METHYLNITRAMINE

BACKGROUND OF THE INVENTION

Methylnitramine (MNA) is represented by the formula $CH_3NHNO_2$.

This is a powerful explosive, stronger than tetryl but weaker than cyclonite. It has, however, been of no practical value chiefly because its preparation is too expensive, requiring first the conversion of methylamine into urethane and then into its nitro derivative. On hydrolysis the latter yields methylnitramine. Similarly, the hydrolysis of dinitrodimethyloxamide leads to the formation of methylnitramine.

Methylnitramine is very readily soluble in water, alcohol, chloform and benzene but is less soluble in ether. It is a strong acid which easily forms salts, including explosive ones. It is not decomposed by boiling water, even in the presence of alkalis, but it is liable to destructive distillation yielding dimethylnitramine $(CH_3)_2N-NO_2$, m.p. 57° C., methyl alcohol, nitrous oxide and many other products.

Methylnitramine decomposes explosively in contact with concentrated sulfuric acid. It is evolved when aniline reacts with tetryl; a diphenylamine derivative is produced simultaneously. Methylnitramine reacts with picryl chloride to form tetryl.

Hereinafter the compound shall be referred to as MNA.

In the prior art methods of preparation of MNA have been excessively expensive because the yields are so low. Yields in the prior art range from about 27% to 39%.

These levels of yield can be drastically improved by the method of the instant invention.

In the prior art 1,3-dimethyl-1,3-dinitrourea from dimethylurea is prepared as follows:

1,3-Dimethyl-1,3-dinitrourea, $H_3CN(NO_2)CO.N(NO_2).CH_3$, mw 178.11, N 31.46%; liq, cap sensitive but insensitive to shock and friction; was prepared by nitrating the parent compound below 30° with concentrated nitric acid or with a mixture of $HNO_3$ and $Ac_2O$.

Explosive compositions of DMDU consist of: ammonium nitrate (AN) 60, ammonium perchlorate 30 and DMDU 10% (more powerful in ballistic mortar test than TNT); or AN 82, DMDU 16 and nitrocellulose (NC) 2%. A colloidal plastic compound is comprised of DMDU 31, NG 15, NC 4 and AN 50% or I 33, NC 5, AN 45 and ammonium perchlorate 17%. A propellant compound is DMDU 43, NC 50 and Ethyl Centralite 7% (Ref 4) (Compare with N,N'-dimethyl-N,N'-diphenylurea, called Centralite 2, described in Vol 2 of Encycl Explosives and Related Items, p. C137-L).

SUMMARY OF THE INVENTION

In summary the instant invention comprises a method of using 1,3-dimethylurea as a starting material. This dimethylurea with or without a solvent is nitrated by the use of strong mixed acids, usually nitric acid and sulfuric acid. The temperature during addition of the mixed and is maintained in the general temperature range of about $-20°$ C. to $+20°$ C.

In summary dimethylurea is nitrated with mixed sulfuric acid and nitric acid. This forms two phases. The nitrated product is separated by solvent extraction. Trace acids are removed by a washing with a strong base solution. A number of water washes may follow. This results in 1,3-dimethyl-1,3-dinitrourea (DMDU) in a solvent. The DMDU with a suitabe solvent present may then be hydrolyzed in situ with hot water to yield methylnitramine (MNA) in water or with hot aqueous formaldehyde to yield 2-nitro-2-aza-1-propanol (NAP) in water. The MNA may then be solvent extracted.

Accordingly, it is one object of the invention to provide an improved method for the preparation of methylnitramine.

It is also one important object of the invention to provide a method of using 1,3-dimethylurea as a starting material for the nitration reaction with certain mixed acids, including nitric acid and sulfuric acid.

It is another important object of the invention to provide a novel method for the preparation of 2-nitro-2-aza-1-propanol from dimethyl dinitrourea.

It is one further object of the invention to provide a method of dissolving 1,3-dimethylurea in an appropriate organic solvent before nitration with mixed acid in order to facilitate addition to mixed acid and especially to increase the yield of the nitration reaction significantly.

Having stated the principal objects of the invention the following is a detailed description of the invention.

DETAILED DESCRIPTION OF THE PREFERRED EMBODIMENT

1. Preparation of Dimethyldinitrourea

A solution containing 40.6 g of 1,3-dimethylurea (DMU), neat or dissolved in up to 80 ml of chloroform or methylene chloride was slowly added to a vigorously stirred mixed acid solution (134.6 g) or to a mixture of mixed acid and up to 80 ml chloroform on methylene chloride which had been previously cooled to $-5°$ C. The temperature of the reaction mixture was maintained at $-10°$ to $+8°$ C. by the controlled rate of addition. After the DMU addition was completed the reaction mixture was added to ice water. The organic layer was separated from the spent acid, the water phase was extracted once with 50 ml of chloroform. Separation and extraction of organic phase may also be accomplished without first drowning the reaction mixture in ice water. The organic phases were washed with 100 ml of aqueous sodium carbonate (14%). The aqueous layer was basic after the washing operation, therefore no additional washing was required. The results from thirteen DMU nitrations are shown in Table 1.

Nitration of 1,3-dimethyl urea:

In the first step (a) nitric acid is the actual nitrating agent: example

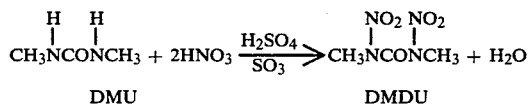

DMU                                DMDU

The sulfuric acid is a catalyst and is not consumed in the process. It aids the nitric acid in doing its job. Since water is generated during the nitration step, sulfur trioxide ($SO_3$) is generally present in the mixed acid.

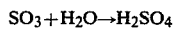

The sulfur trioxide consumes the water generated in the reaction. The nitration will proceed without the $SO_3$ but a larger amount of mixed acid would be required. A significant increase in yield of this reaction occurs when DMU is first dissolved in an appropriate solvent. This is because the DMU and the product DMDU remain in the organic solvent phase while the sulfuric acid remains in the immiscible mixed acid phase. Sulfuric acid can catalytically decompose DMDU resulting in reduced yield.

Increased yields are also realized when a DMU solution is added to a mixture of mixed acid and halogenated organic solvent, preferably chloroform or methylene chloride.

Separation of DMDU

Procedure I (hydrolysis of neat DMDU)

To a 3 neck 2 liter flask equipped with a reflux condenser, a magnetic stirrer and addition funnel was added to 200 ml of water. To the refluxing water was added 233.7 g of DMDU over a 30 minute period. The aqueous solution was refluxed for an additional 20 minutes and after cooling extracted 4 times with 100 ml portions of methylene chloride. The organic phase was dried with molecular sieves overnight. On evaporation of the $CH_2Cl_2$ 138.4 g (69%) of white needle crystals was obtained.

TABLE I

| | | | Nitration of 1,3-Dimethlurea (DMU) with Mixed Acid | | | |
|---|---|---|---|---|---|---|
| Batch # | DMU wt. | Solvent | Mixed Acid/ Solvent Comb. | Extractions (Solvent) | Reaction Temp. | Crude DMDU yield |
| B-1 | 22.0 g | — | 98.8 g MA + 50 ml $CH_2Cl_2$ | 1 × 50 ml $CH_2Cl_2$ | 0°–+8° C. | 24.2 g 54.4% |
| 10-3 | 40.6 g | 80 ml $CHCl_3$ | 178.6 g MA - no solvent | 1 × 50 ml $CHCl_3$ | −10°–0° C. | 55.9 g 68.1% |
| 10-4 | 40.6 g | — | " | 2 × 50 ml $CHCl_3$ | −2°–+1° C. | 40.1 g 46.8% |
| 10-5 | 40.6 g | 80 ml $CH_2Cl_2$ | " | 1 × 50 ml $CH_2Cl_2$ | −1°–+1° C. | 45.0 g 54.8% |
| 10-6 | 40.6 g | 80 ml $CH_2Cl_2$ | 178.6 g MA + 80 ml $C_7H_{16}$ | 1 × 50 ml $CH_2Cl_2$ | −5°–0° C. | 52.1 g 63.5% |
| 10-7 | 40.6 g | 80 ml $CHCl_3$ | 178.6 g MA - no solvent | 1 × 50 ml $CHCl_3$ | 0°–+7° C. | 53.3 g 64.9% |
| 10-8 | 40.6 g | 80 ml $CHCl_3$ | 134.3 g MA - no solvent | 1 × 50 ml $CHCl_3$ | −2°–0° C. | 62.4 g 76.0% |
| 10-9 | 40.6 g | 80 ml $CHCl_3$ | 110 g MA - no solvent | 1 × 50 ml $CHCl_3$ | −3°–0° C. | 52.0 g 63.4% |
| 10-11 | 40.6 g | 80 ml $CHCl_3$ | 178.6 g MA - no solvent | 1 × 50 ml $CHCl_3$ | −20°–−5° C. | not available |
| 10-12 | 20.3 g | 40 ml $CHCl_3$ | 50.3 g MA - no solvent | 1 × 25 ml $CH_2Cl_2$ 1 × 25 ml $CHCl_3$ | −6°–+1° C. | 21.0 g 51.2% |
| 10-13 | 40.6 g | 80 ml $CHCl_3$ | 135.2 g MA - no solvent | 2 × 50 ml $CHCl_3$ | −2°–+4° C. | 55.1 g 67.1% |
| 11-1 | 40.6 g | 80 ml $CHCl_3$ | 178.6 g MA + 50 ml $CH_2Cl_2$ | 1 × 50 ml $CH_2Cl_2$ 1 × 50 ml $CHCl_3$ | −5°–−2° C. | 54.1 g 65.9% |
| 12-1 | 9.0 g | 20 ml $CHCl_3$ | 59.9 g of 98% $HNO_3$ - no solvent | 1 × 30 ml $CH_2Cl_2$ | −5°–0° C. | 6.8 g 37.4% |
| 13-1 | 14.7 g | 30 ml $CHCl_3$ | 85 g 98% $HNO_3$ + 85 g $AC_2O$ no solvent | 1 × 50 ml $CH_2Cl_2$ | −5°–+2° C. | 21.0 g 70.7% |

DMDU - 1,3-dimethyl-1,3-dinitrourea
Mixed Acid (MA) - 47.1% actual $H_2SO_4$, 55.7% actual $HNO_3$, 0.4% nitrogen oxides, and −3.0% $H_2O$ The use of sulfuric acid permits one to separate the product (1,3-dimethyl-1,3-dinitrourea) from the used acid because two phases are formed.

Purification of DMDU:

The product must be purified prior to the hydrolysis step, because trace amounts of sulfuric in the water during the hydrolysis step with decompose the methylnitramine as it forms:

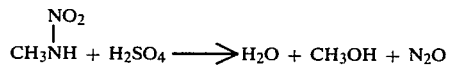

Removal of sulfuric acid is effected by washing of the organic liquid phases with 14% aqueous sodium carbonate. Optional additional water washes will improve purity of DMDU.

2. Hydrolysis of DMDU

The DMDU solution may be hydrolysed in situ, or if the solvent is distilled off under ambient or reduced pressure, up to 62.4 g DMDU (76%) is obtained.

Procedure II (Hydrolysis of DMDU solution, in situ solvent removal)

To the above equipment is added a Dean-Stark Moisture Receiver to facilitate organic solvent removal. The above described chloroform solution of DMDU is added to an amount of boiling water approximately equal in weight to the DMDU in the solution at a rate where the water continues to boil. The chloroform is distilled off continuously. The Dean-Stark Trap is designed to separate the chloroform phases from the water phase and return the water to the distillation pot.

The remainder of the procedure is the same procedure I.

Procedure III (Preparation of 2-Nitro-2-aza-1-propanol (NAA) by in situ hydrolysis of DMDU in aqeous formaldehyde):

The hydrolysis of DMDU in boiling 37% aqueous formaldehyde yields 2-nitro-2-aza-1-propanol. The formula for this reaction is:

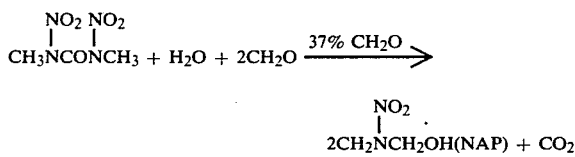

$$2CH_2NCH_2OH(NAP) + CO_2$$

The DMDU maybe hydrolyzed exactly as outlined in Procedure I or procedure II, except that aqueous formaldehyde is used instead of water. The resulting NAP is recovered according to the procedure set forth by Gareen, et at in Zhurnal Org, Khim, Vol. 7, p. 623–624 (1971) (English Translation).

The following table gives a number of illustrative examples of the invention.

Table I illustrates the nitration of dimethylurea.

Hydrolysis of 1,3-dimethyl-1,3-dinitrourea to yield methylnitramine

During the hydrolysis no sulfuric acid should be present because methylnitramine is decomposed by trace amounts of sulfuric acid.

To speed up the reaction of DMDU with water, the reaction mixture is heated to 70° to 100° C.:

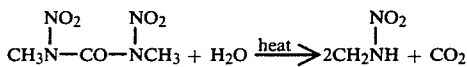

The solvent is removed by distillation during the hydrolysis step. The purpose of dissolving the DMDU in organic solvent is also to desensitize it, so that it will be safe to handle.

Separation of methylnitramine from water

Methylnitramine is highly soluble in water. Therefore it must be extracted with an organic solvent. The organic solvents that are preferred are chloroform and methylene chloride.

The solvents that may be used in the nitration step are usually halogenated solvents that may be selected from the group consisting of methylene chloride and chloroform. Other well known halogenated solvents which have boiling points below 100° C. may be used.

The nitration step is always performed with a mixture of nitric acid and sulfuric acid. The concentration of nitric acid in the mixed acid is usually in the range of 30% to 70% and most preferably 40% to 60%. The range of 40 to 60% nitric acid is preferred. The sulfuric acid may vary in concentration from about 30% to 70% but is not critical. The ratio of volume of nitric acid to sulfuric acid is in the range of 3 to 1 to 1 to 3 and most preferably 1 to 1 to 2 to 1.

The temperature range of the nitration reaction is in the broad range of −20° C. to +20° C. The most preferred temperature range is in the range of −5° C. to 0° C. and is considered critical to a high yield position. In other words a consistently high yield cannot be obtained unless the temperature range of −5° C. to 0° C. is maintained in the nitration step.

The weight ratio of solvent to the starting material, dimethylurea is in the range of 1 to 1 to 5 to 1, preferably from 2.5 to 1 to 3.5 to 1 to insure an excess of solvent.

The hydrolysis may be done on purified DMDU or in situ by the use of hot water. The hot water be in the range of 70° C. to 100° C., most preferably 95° C. to 100° C. up to the boiling point of water.

The use of 37% aqueous formaldehyde in place of water with no other changes in the hydrolysis procedure will produce 2-nitro-2-aza-1-propanol from DMDU or in situ from the DMDU solution.

To those skilled in the art, many modifications and variations of the present invention are possible in light of the above teachings. It is therefore to be understood that the present invention can be practiced otherwise than as specifically described herein and still be within the spirit and scope of the appended claims.

What is claimed is:

1. A process for the production of methylnitramine comprising:
   (a) preparation of 1,3-dimethyl-1,3-dinitrourea using a mixture of nitric and sulfuric acid and dimethylurea to yield the nitrated dimethylurea;
   (b) separation of 1,3-dimethyl-1,3-dinitrourea from the spent acids (used) after the nitration step has been completed by the use of an organic solvent selected from the group consisting of chloroform and methylene chloride;
   (c) purification of 1,3-dimethyl-1,3-dinitrourea by washing with an aqueous solution contain an organic bottom phase that yields a two phase mixture with nitrated product in the bottom phase;
   (d) taking the bottom phase and mixing this phase with hot water to yield a two phase mixture;
   (e) removal of the bottom phase from step d that contains dimethyl dinitrourea in the organic solvent;
   (f) hydrolysis of the dimethyldinitrourea in the organic solvent wth hot water to yield methylnitramine.

2. A method for the preparation of methylnitramine comprising the steps of:
   (a) starting with dimethylurea;
   (b) mixing dimethylurea with a solvent;
   (c) nitrating with a mixture of nitric and sulfuric acids to obtain 1,3-dimethyl-1,2-dinitrourea;
   (d) removal of 1,3-dimethyl-1,3-dinitrourea from mixed acid by separation of an immicible liquid phase;
   (e) washing and neutralizing the nitration reaction product with an inorganic base;
   (f) in Situ hydrolysis with hot water and concurrent removal of solvent by distillation;
   (g) separating of methylnitramine from water by extraction with a halogenated solvent selected from the group consisting of methylenechloride and chloroform.

3. The method of claim 2 wherein the composition of nitric acid in the mixed acid is between 40% and 60% based upon the total weight of the mixture.

4. The method of claim 2 wherein the temperature of the nitration reaction is between −20° C. and 20° C.

5. The method of claim 2 wherein the temperature range in the nitration reaction is in the range of −5° C. to 0° C.

6. The method of claim 4 wherein the ratio of nitric acid to sulfuric acid is in the range of 3 to 1 to 1 to 3.

7. The method of claim 4 wherein the weight ratio of solvent to dimethylurea is in the range of 1 to 1 to 5 to 1.

8. The method of claim 7 wherein the weight ratio of solvent to dimethyl urea is between 2.5 to 1 and 3.5 to 1.

9. The method of claim 2 wherein the temperature of water is in the range of 70° C. to 100° C.

10. The method of claim 9 wherein the temperature of the water is in the range of 95° C. to 100° C.

11. The method of claim 10 wherein the final hydrolysis step is performed in boiling 37% aqueous formaldehyde to yield directly 2-nitro-2-aza-1-propanol by in situ hydrolysis and in situ reaction of methylnitramine with formaldehyde.

12. A method for the production of methylnitramine comprising the steps of:
 (1) adding dimethylurea to an organic solvent selected from the group consisting of chloroform and methylene chloride,
 (2) nitrating the N,N'-dimethylurea in the solvent with a mixed acid comprising $HNO_3$ and $H_2SO_4$ at a temperature in the range of −20° C. to 20° C. to produce N,N'-dimethyl-N,N'-dinitrourea, in solution,
 (3) extracting N,N'-dimethyl-N,N'-dinitrourea by the use of the organic solvent to form N,N'-dimethyl-N,N'-dinitrourea extract in solution,
 (4) washing the extract of N,N'-dimethyl-N,N'-dinitrourea in solution with an aqueous base
 (5) hydrolyzing the N,N'-dimethyl-N,N'-dinitrourea extract in the organic solvent by mixing the N,N'-dimethyl-N,N'-dinitrourea extract from step 4 with hot water,
 (6) isolating the methynitramine by extracting with an organic solvent.

* * * * *